United States Patent
An

(10) Patent No.: US 7,527,603 B2
(45) Date of Patent: May 5, 2009

(54) OZONE TREATMENT APPARATUS USING OZONE GAS

(76) Inventor: Sun-Tae An, 804-1904, Lotte-Castle Apt., 1049, Guseo 2-Dong, Geumjeong-Gu, Busan 609-751 (KR)

( * ) Notice: Subject to any disclaimer, the term of this patent is extended or adjusted under 35 U.S.C. 154(b) by 159 days.

(21) Appl. No.: 11/699,106

(22) Filed: Jan. 29, 2007

(65) Prior Publication Data
US 2008/0045874 A1 Feb. 21, 2008

(30) Foreign Application Priority Data
Aug. 21, 2006 (KR) .................. 20-2006-0022390 U

(51) Int. Cl.
*A61M 37/00* (2006.01)
(52) U.S. Cl. .................. 604/25; 604/289; 604/290; 604/304; 604/305
(58) Field of Classification Search .................. 604/23, 604/25, 289, 290, 293; 422/33; 186.07; 602/2, 602/48
See application file for complete search history.

(56) References Cited

U.S. PATENT DOCUMENTS

| | | | | |
|---|---|---|---|---|
| 3,907,389 A * | 9/1975 | Cox et al. | ...... | 312/1 |
| 5,098,415 A * | 3/1992 | Levin | ...... | 604/293 |
| 5,154,697 A * | 10/1992 | Loori | ...... | 604/23 |
| 5,810,758 A * | 9/1998 | Yamazaki et al. | ...... | 604/264 |
| 6,060,020 A * | 5/2000 | Piuk et al. | ...... | 422/33 |
| 6,286,235 B1 * | 9/2001 | An | ...... | 36/132 |
| 6,432,077 B1 * | 8/2002 | Stenzler | ...... | 604/23 |
| 6,572,594 B2 * | 6/2003 | Satterfield et al. | ...... | 604/290 |
| 6,620,379 B1 * | 9/2003 | Piuk et al. | ...... | 422/3 |
| 7,122,018 B2 * | 10/2006 | Stenzler et al. | ...... | 604/23 |
| 2003/0139734 A1 * | 7/2003 | Liang | ...... | 606/2 |
| 2008/0132825 A1 * | 6/2008 | Rasor et al. | ...... | 604/23 |

* cited by examiner

*Primary Examiner*—Kim M Lewis
(74) *Attorney, Agent, or Firm*—Park & Associates IP Law LLC

(57) ABSTRACT

The present invention relates to an ozone treatment apparatus using ozone gas, in which the ozone gas is directly injected to a lesion of the human body by utilizing the sterilizing power caused by oxidation of ozone gas, so that the lesion can be sterilized and stanched to relieve the pain in the lesion, thereby maximizing therapeutic effect by the ozone irrespective of the shape of bodily regions having the lesion and the kind of lesion, and so that the treatment using ozone gas can be readily conducted, thereby improving convenience in use as well as significantly reducing the cost and time spent for the treatment.

2 Claims, 4 Drawing Sheets

OZONE TREATMENT APPARATUS USING OZONE GAS

FIELD OF THE INVENTION

The present invention relates to an ozone treatment apparatus using ozone gas, and more particular, to an ozone treatment apparatus using ozone gas, in which the ozone gas is directly injected to a lesion of the human body by utilizing the sterilizing power caused by oxidation of ozone gas, so that the lesion can be sterilized and stanched to relieve the pain in the lesion, thereby maximizing therapeutic effect by the ozone irrespective of the shape of bodily regions having the lesion and the kind of lesion, and so that the treatment using ozone gas can be readily conducted, thereby improving convenience in use as well as significantly reducing the cost and time spent for the treatment.

BACKGROUND OF THE INVENTION

Generally, despite the fact that ozone plays harmful roles such as causing respiratory diseases and the like in the human body, inhibiting the growth of the plant and the like, conventional ozone treatment apparatuses have been widely used since ozone has several advantages in that various kinds of wounds due to trauma can be sterilized and stanched to relieve the pain in the lesion as well as various kinds of skin diseases such as athlete's foot and the like caused by funguses or viruses can be treated by means of the strong sterilizing power of the ozone only by taking care of safe handling of ozone.

As shown in FIG. 1, the conventional ozone treatment apparatus comprises a sealing body 10 having an inlet opening formed thereon for allowing a lesion such as a hand, a foot or the like to be put in and out therethrough, the sealing body 10 being composed of an inner sealing body 10b having a plurality of ozone gas through-holes 10c formed thereon and an outer sealing body 10a; a supply passageway 12 constructed so as to communicate with one side which is formed by dividing the space between the outer and inner sealing bodies 10a and 10b into two parts, for supplying ozone gas therethrough; a recovery passageway 14 constructed so as to communicate with the other side of the space for recovering the residual ozone after ozone treatment, the supply and recovery passageways 12 and 14 being connected to an ozone generator(not separately shown, since having a typical configuration); and a band 18 installed at the inlet opening of the sealing body 10 for preventing the ozone gas from being discharged to the outside. However, the conventional ozone treatment apparatus has problems in that when ozone is fed to the sealing body 10 more than required, the inside of the sealing body 10 is pressurized to thereby frequently induce leakage of the ozone gas, as well as a pair of closed cycles are formed by the sealing body 10 and the supply passageway 12 and by the sealing body 10 and the recovery passageway 14, respectively, to thereby generate moisture inside the sealing body 10, so that the therapeutic effect by the ozone is decreased, in that the space between the outer and inner sealing bodies 10a and 10b has to be filled with the ozone gas, so that much time is necessary for the ozone treatment, and in that blood circulation to the lesion is prohibited by the band 18 to thereby impede regeneration of the lesion, so that the therapeutic effect is decreased to deteriorate the lesion.

Besides the conventional ozone treatment apparatus as described above, other various kinds of ozone treatment apparatuses have been developed, but there are still disadvantages in that they cannot completely solve problems of the conventional ozone treatment apparatus and their construction are complicated, thereby causing inconvenience in use as well as increasing the manufacturing cost, in that the generating quantity of the ozone is extremely small in case where an ozone treatment apparatus is simplified in its configuration, thereby significantly decreasing the therapeutic effect by the ozone, and in that it has to be replaced with a new one each time it is used in case of a disposable ozone treatment apparatus, thereby uneconomically increasing the treatment cost. Therefore, an ozone treatment apparatus needs to be developed in order to solve the above-described problems of the conventional prior arts.

SUMMARY OF THE INVENTION

Accordingly, the present invention has been made in view of the above-mentioned problems occurring in the prior art, and it is an object of the present invention to provide an ozone treatment apparatus using ozone gas, in which ozone gas is directly injected to a lesion of the human body by utilizing the sterilizing power caused by oxidation of ozone gas, so that the lesion can be sterilized and stanched to relieve the pain in the lesion, thereby maximizing therapeutic effect by the ozone irrespective of the shape of bodily regions having the lesion and the kind of lesion, and so that the treatment using ozone gas can be readily conducted, thereby improving convenience in use as well as significantly reducing the cost and time spent for the treatment.

In order to accomplish the above objects, according to the present invention, there is provided an ozone treatment apparatus using ozone gas which comprises an ozone generator connectively mounted to an oxygen feed tank for supplying oxygen, a supply pipe linkably connected to the ozone generator and adapted to supply ozone to a lesion therethrough, and a recovery pipe for recovering the residual ozone remaining after ozone treatment therethrough, wherein the improvement comprising: a cover plate connected to an end portion of the supply pipe so as to be closely seated on the lesion and adapted to cover the lesion; a disposable gauze having ozone resistance and disinfection property, the disposable gauze being adhered to the lesion on which the cover plate is seated and adapted to freely transmit ozone gas therethrough; a dome-shaped hood disposed at a circumferential end thereof around the outermost periphery of the cover plate and connected at a top end thereof to the recovery pipe in such a manner as to fluidically communicate with the recovery pipe; and an exhaust pipe including an ozone decomposition device and a blower mounted thereon and adapted to fluidically communicate with the recovery pipe.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE INVENTION

Hereinafter, the transparent ornament of the present invention will be described in detail with reference to the appended drawings.

Figure 1:
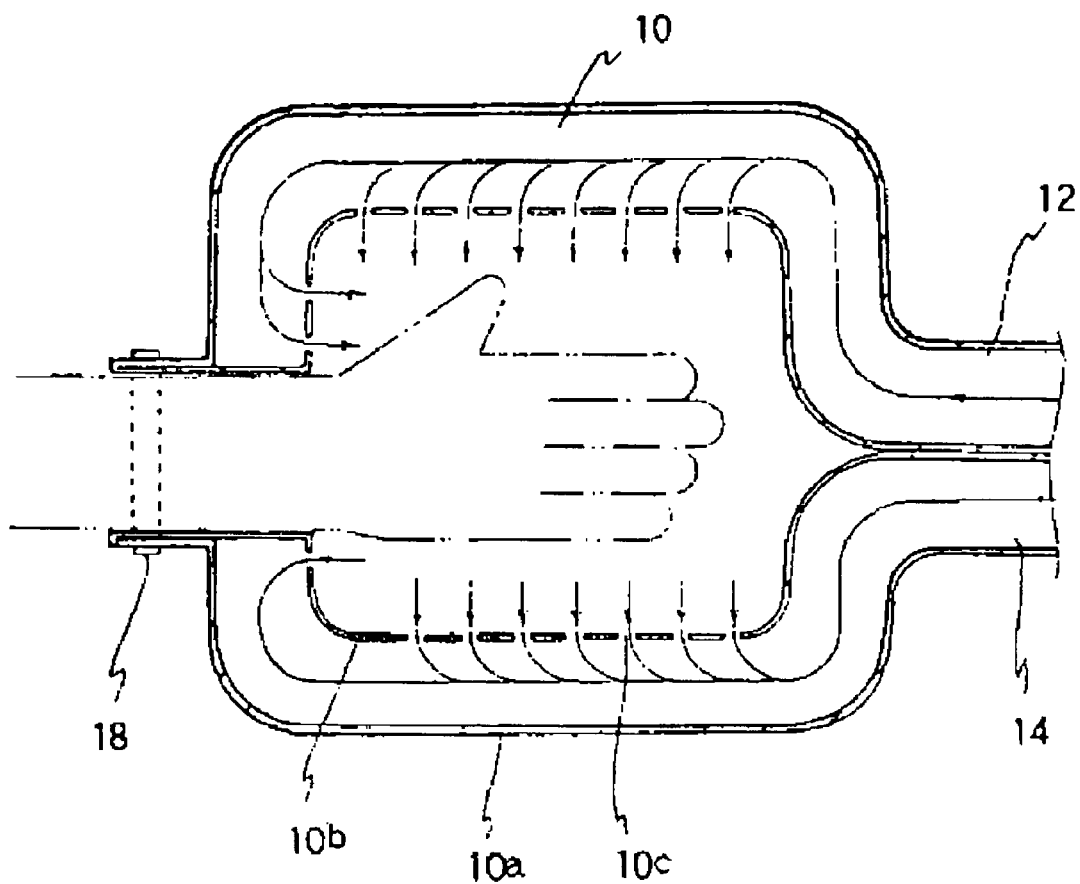
FIG. 1 is a cross-sectional view showing an embodiment of a conventional ozone treatment apparatus.
Figure 2:
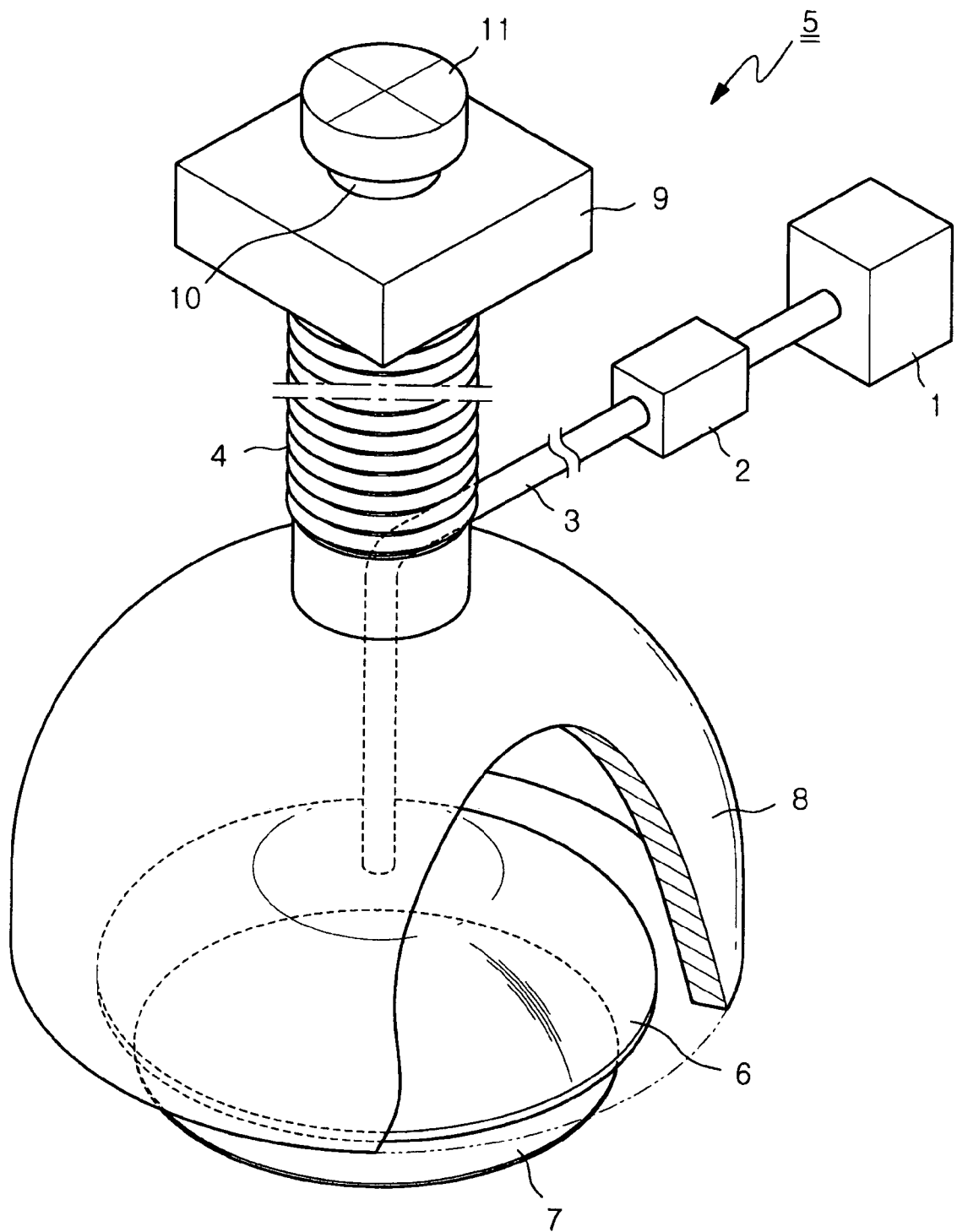
FIG. 2 is a perspective view showing a preferred embodiment of an ozone treatment apparatus according to the present invention.
Figure 3:
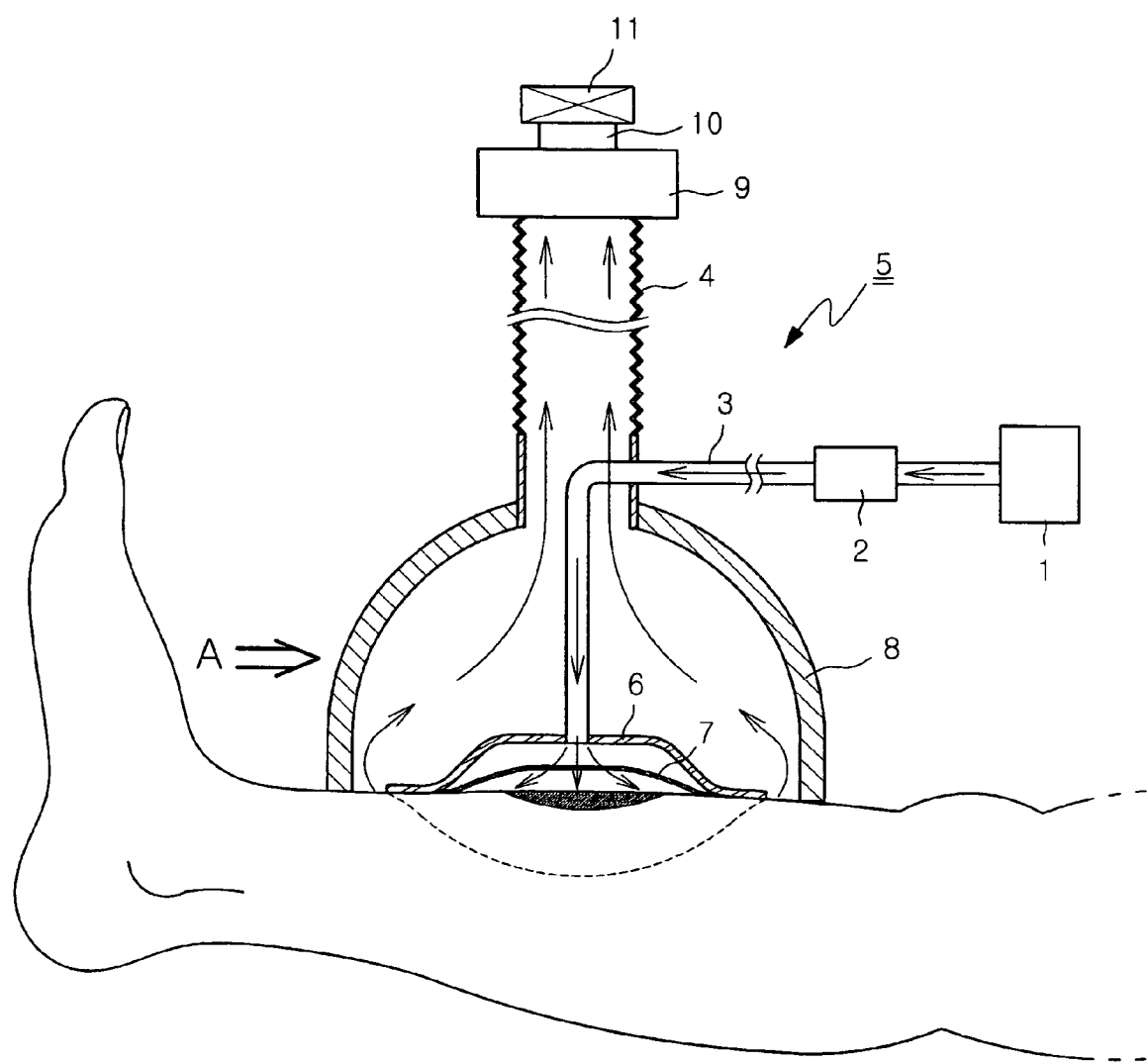
FIG. 3 is a cross-sectional configuration view showing an operation of the ozone treatment apparatus according to the present invention.
Figure 4:
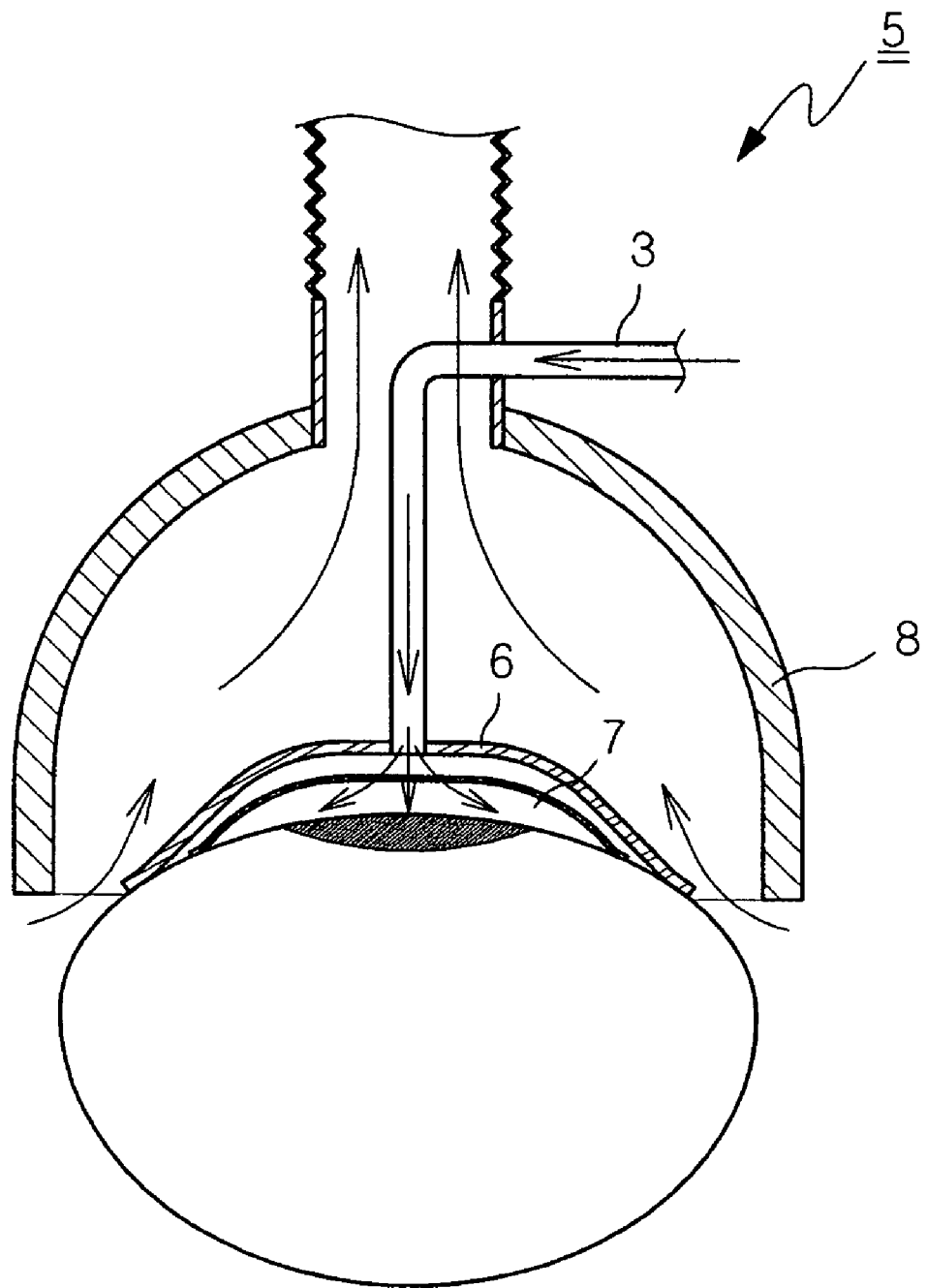
FIG. 4 is a cross-sectional configuration view showing an operation of the ozone treatment apparatus according to the present invention as viewed from an arrow A direction of FIG. 3.

FIG. 2 is a perspective view showing a preferred embodiment of an ozone treatment apparatus according to the present invention and FIG. 3 is a cross-sectional configuration view showing an operation of the ozone treatment apparatus according to the present invention. Although the same reference numerals are used in description of configuration of the conventional prior art and the present invention, they denote different constitutional elements.

A typical ozone treatment apparatus 5 according to the present invention comprises an ozone generator 2 connectively mounted to an oxygen feed tank 1 for supplying oxygen, a supply pipe 3 linkably connected to the ozone generator 2 and adapted to supply ozone to a lesion therethrough, and a recovery pipe 4 for recovering the residual ozone remaining after ozone treatment therethrough.

In the above construction of the typical ozone treatment apparatus, the ozone treatment apparatus according to the present invention is characterized by comprising: a cover plate 6 fixably mounted to an end portion of the supply pipe 3 connected to the ozone generator 2 so as to allow the ozone generated from the ozone generator 2 to be directly injected to the lesion through the supply pipe 3 irrespective of the shape of bodily regions having the lesion, the cover plate 6 being closely seated on the lesion and freely deformed; and a disposable gauze 7 having ozone resistance and disinfection property, the disposable gauze 7 being adhered to the lesion, that is, below the cover plate 6 and adapted to freely transmit ozone gas therethrough. At this time, a packing molded of silicon is preferably used as the cover plate 6.

The ozone treatment apparatus according to the present invention further comprises: a dome-shaped hood 8 disposed at a circumferential end thereof around the outermost periphery of the cover plate 6 and connected at a top end thereof to the recovery pipe 4 in such a manner as to fluidically communicate with the recovery pipe 4; and an exhaust pipe 10 including an ozone decomposition device 9 and a blower 11 mounted thereon and adapted to fluidically communicate with the recovery pipe 4. The ozone decomposition device 9 is installed at the upper end of the recovery pipe 4 so as to fluidically communicate with the exhaust pipe 10, and the blower 11 is installed at the upper end of the exhaust pipe 10 and adapted to discharge the residual ozone remaining after ozone treatment to the outside.

Further, the supply pipe 3 for supplying ozone gas therethrough passes through a side of the recovery pipe 4 and connected to the cover plate 6 which is disposed inside the hood 8. A part of the recovery pipe 4 is formed into a cymbal shape having its flexibility, so that the recovery pipe 4 can be freely disposed at bodily regions having a lesion.

The ozone treatment apparatus 5 constructed as described above operates ozone treatment at a time of being injured on a bodily region. Hereinafter, the operation of the ozone treatment apparatus 5 will be described in detail.

First, the disposable gauze 7 having ozone resistance is adhered to the lesion intended to operate the ozone treatment, the cover plate 6 is seated on the lesion, more preferably on the gauze 7, and then hood 8 is seated at a circumferential end thereof around the lesion in such a manner as to surround around the outermost circumference of the cover plate 6. For reference, when the hood 8 is seated around the lesion, it is seated so as to allow the outside air to be ventilated to the inside of the hood 8 therethrough. But, if the hood 8 does not have a space defined therein to ventilate air, it preferably has a plurality of ventilation holes formed thereon.

Further, when ozone is fed to the inside of the cover plate 6, by which the lesion is sealed, via the supply pipe 3 by operating the ozone generator 2 connectively mounted to an oxygen feed tank 1, the ozone is fed to the lesion through the disposable gauze 7 having ozone resistance, whereby ozone treatment can be operated as well known.

A part of ozone which might be leaked from the gap between the cover plate 6 and the lesion during the ozone treatment is operating is decomposed while passing through the ozone decomposition device 9 via the cymbal-shaped recovery pipe 4, and then is ventilated via the exhaust pipe 10 by means of the blower 11. After the ozone treatment is completed, oxygen is fed to the lesion from the oxygen feed tank 1 until the residual ozone remaining inside cover plate 6, which have been used for the ozone treatment operated in the lesion, is converted into oxygen. Meanwhile, the residual and leaked ozone remaining in the inside of the hood 8 and the outside of the cover plate 6 sequentially passes through the hood 8, the recovery pipe 4 and the exhaust pipe 10 having the blower 11 installed therein in this order, and then is discharged as described above. Simultaneously, while the blower 11 is operated, the outside atmospheric pressure is applied to a ventilation space between the hood 8 and the lesion.

As described above, according to the ozone treatment apparatus using ozone gas of the present invention, ozone gas is directly injected on a lesion of the human body by utilizing the sterilizing power caused by oxidation of ozone gas, so that the lesion can be sterilized and stanched to relieve the pain in the lesion, thereby maximizing therapeutic effect by the ozone irrespective of the shape of bodily regions having the lesion and the kind of lesion, and so that the treatment using ozone gas can be readily conducted, thereby improving convenience in use as well as significantly reducing the cost and time spent for the treatment.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. An ozone treatment apparatus using ozone gas which comprises an ozone generator connected to an oxygen feed tank for supplying oxygen, a supply pipe connected to the ozone generator and adapted to supply ozone to a lesion, and a recovery pipe for recovering the residual ozone remaining after ozone treatment, wherein the improvement comprises:
   a cover plate connected to an end portion of the supply pipe adapted to be closely seated on and cover the lesion;
   a disposable gauze having ozone resistance and disinfection property, the disposable gauze adapted to be adhered to the lesion on which the cover plate is seated and adapted to freely transmit ozone gas therethrough;
   a dome-shaped hood disposed around the outermost periphery of the cover plate and connected to the recovery pipe in fluid communication with the recovery pipe; and
   an exhaust pipe having an ozone decomposition device and a blower connected to the exhaust pipe and in fluid communication with the recovery pipe.

2. An ozone treatment apparatus of claim 1, wherein the recovery pipe is expandable in a longitudinal direction.

* * * * *